US008444701B2

(12) United States Patent
Bloebaum et al.

(10) Patent No.: US 8,444,701 B2
(45) Date of Patent: May 21, 2013

(54) ANTIMICROBIAL CONTAINMENT CAP FOR A BONE ANCHORED PROSTHESIS MOUNTING

(75) Inventors: Roy D. Bloebaum, Salt Lake City, UT (US); Kent N. Bachus, Salt Lake City, UT (US); Raymond E. Olsen, Smithfield, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1287 days.

(21) Appl. No.: 11/995,886

(22) PCT Filed: Jul. 19, 2006

(86) PCT No.: PCT/US2006/028115
§ 371 (c)(1),
(2), (4) Date: Sep. 11, 2008

(87) PCT Pub. No.: WO2007/013948
PCT Pub. Date: Feb. 1, 2007

(65) Prior Publication Data
US 2009/0005820 A1    Jan. 1, 2009

Related U.S. Application Data

(60) Provisional application No. 60/701,229, filed on Jul. 20, 2005.

(51) Int. Cl.
*A61F 2/60* (2006.01)
*A61F 2/78* (2006.01)
*A61F 2/80* (2006.01)

(52) U.S. Cl.
USPC .............................................. 623/32; 623/36

(58) Field of Classification Search
USPC ................ 606/54, 302; 623/32–37; 604/174
See application file for complete search history.

(56) References Cited

U.S. PATENT DOCUMENTS

| | | | |
|---|---|---|---|
| 3,947,897 A | | 4/1976 | Owens |
| 4,143,426 A | * | 3/1979 | Hall et al. ....................... 623/53 |
| 4,158,895 A | * | 6/1979 | Frosch et al. ................... 606/60 |
| 4,516,968 A | * | 5/1985 | Marshall et al. ............... 604/174 |
| 4,856,504 A | * | 8/1989 | Yamamoto et al. ............. 606/59 |
| 4,897,081 A | * | 1/1990 | Poirier et al. ................... 604/175 |
| 5,137,520 A | * | 8/1992 | Maxson et al. ................ 604/180 |
| 5,207,652 A | * | 5/1993 | Kay .............................. 604/180 |
| 5,352,204 A | * | 10/1994 | Ensminger ............... 604/288.03 |
| 5,447,492 A | * | 9/1995 | Cartmell et al. ................ 602/58 |
| 5,662,715 A | | 9/1997 | Slemker |

(Continued)

*Primary Examiner* — Kevin T Truong
*Assistant Examiner* — David Bates
(74) *Attorney, Agent, or Firm* — Michael Best & Friedrich LLP

(57) ABSTRACT

An antimicrobial containment cap is provided for use in a bone anchored prosthesis mounting system of the type having an externally protruding fixator pin carried by all implanted bone anchored mounting post, wherein the fixator pin accommodates removable attachment to an exoskeletal prosthesis such as a prosthetic limb or the like for an amputee. The containment cap, when mounted onto the fixator pin, is interposed between the prosthesis and soft tissue covering the end or stump of an amputated residual limb or the like. The containment cap carries and supports a selected antimicrobial or antibacterial agent in substantial contact with the soft stump tissue in a position closely overlying and substantially circumscribing the tissue interface with the externally protruding fixator pin to safeguard against infection. The containment cap is adapted for quick and easy periodic removal for cleaning and/or replenishment of the antimicrobial agent.

12 Claims, 4 Drawing Sheets

U.S. PATENT DOCUMENTS

| | | |
|---|---|---|
| 5,702,388 A * | 12/1997 | Jackson et al. .................. 606/54 |
| 5,800,563 A * | 9/1998 | Arbogast et al. ................ 623/35 |
| 5,888,216 A | 3/1999 | Haberman |
| 6,258,092 B1 * | 7/2001 | Dall .............................. 606/292 |
| 6,438,397 B1 * | 8/2002 | Bosquet et al. ............... 600/310 |
| 6,869,450 B2 * | 3/2005 | Grundei ......................... 623/32 |
| 7,374,577 B2 * | 5/2008 | Kim et al. ...................... 623/32 |
| 2003/0171825 A1 * | 9/2003 | Blunn et al. .................... 623/32 |
| 2004/0243251 A1 * | 12/2004 | Carstens ........................ 623/34 |
| 2005/0256540 A1 * | 11/2005 | Silver et al. ...................... 607/3 |
| 2006/0041318 A1 * | 2/2006 | Shannon .................... 623/23.46 |
| 2007/0032883 A1 * | 2/2007 | Mantelmacher ................ 623/34 |
| 2008/0161739 A1 * | 7/2008 | Brandigi ........................ 602/43 |

\* cited by examiner

ANTIMICROBIAL CONTAINMENT CAP FOR A BONE ANCHORED PROSTHESIS MOUNTING

BACKGROUND OF THE INVENTION

This invention relates generally to improvements in external or exoskeletal prosthetic devices and systems of the type utilizing an implanted, bone anchored mounting post having or carrying an externally protruding or externally exposed fixator structure for removable attachment of a prosthesis such as a prosthetic limb or the like. More particularly, this invention relates to an antimicrobial containment cap for use in combination with a bone anchored prosthesis mounting system, wherein the containment cap supports and retains a selected antimicrobial agent against the skin of an amputee substantially at the exit site or tissue interface of the fixator structure extending through the skin, to reduce or eliminate risk of infection.

Socket type prosthetic limbs such as prosthetic arm and leg structures for use by amputees are generally well known in the art, wherein a prosthesis is constructed with an open-ended and typically padded socket structure for receiving and supporting the post-surgical stump of a residual amputated limb. By way of example, a socket type prosthetic leg includes such open-ended socket structure at an upper end thereof for receiving and supporting the post-surgical upper leg of a transfemoral amputee. Various straps and/or other fasteners are provided for securing the prosthetic leg to the amputated limb to accommodate walking mobility at least on a limited basis. Such prosthetic limbs can be an important factor in both physical and mental rehabilitation of an amputee.

However, socket type prosthetic limbs are associated with a number of recognized limitations and disadvantages. In particular, the socket style prosthesis inherently couples mechanical loads associated with normal ambulatory activity through a soft tissue interface defined by the soft tissue covering the end or stump of the residual amputated limb, but wherein this soft tissue interface is structurally unsuited for this purpose. While many different arrangements and configurations for the requisite straps and other fasteners have been proposed for improved transmission and distribution of these mechanical loads to bone structures for improved secure and stable prosthesis attachment, to correspondingly accommodate a more natural ambulatory movement, such arrangements have achieved only limited success. In addition, compressive loading of this soft tissue interface often results in blisters, sores, chafing and other undesirable skin irritation problems which have been addressed primarily by adding soft padding material within the socket structure. But such soft padding material undesirably increases the extent of the soft or non-rigid interface between the amputated limb and prosthesis, all in a manner that is incompatible with an optimally secure and stable prosthesis connection. As a result, particularly in the case of a prosthetic leg, traditional socket style connection structures and methods have generally failed to accommodate a normal walking motion.

In recent years, improved external or exoskeletal prosthetic devices have been proposed, wherein the external prosthesis is structurally linked by means of a bone anchored mounting system directly to patient bone. In such devices, a rigid mounting post is surgically implanted and attached securely to patient bone as by means of osseointegration or the like. This implanted mounting post extends from the bone attachment site and includes or is attached to a fixator pin or post structure that protrudes through the overlying soft tissue at the end of the residual amputated limb. Thus, one end of the fixator pin is externally exposed for suitable and secure attachment to a prosthetic limb or the like. In such bone anchored mounting systems, mechanical loads on the prosthetic limb during ambulation are transmitted by the rigid components including the external fixator pin and the implanted mounting post directly to patient bone. As a result, conventional mechanical loading of the soft tissue interface is avoided, and substantially improved and/or normal patient movements are accommodated. In addition, the requirement for compressive loading of the soft tissue at the end of the amputated limb is significantly reduced, to correspondingly reduce incidence of blisters and other associated skin irritation problems.

Although use of a bone anchored mounting system offers potentially dramatic improvements in secure and stable prosthetic limb attachment, and corresponding improvements in amputee lifestyle, the exit site or interface between the externally protruding fixator pin and the soft tissue at the end of the residual limb inherently subjects the amputee to a significant and on-going risk of infection. That is, the soft tissue interface with the externally protruding fixator pin is difficult to seal and protect against entry of microbial infection-producing organisms. The difficulties in adequately sealing this tissue-pin interface are compounded by the presence of multiple and typically random and irregular-shaped small skin folds formed in the soft tissue at the end of the residual limb, and thus present in the immediate vicinity of the tissue-pin interface. These small skin folds unfortunately provide multiple shallow channels or pathways which are difficult to keep clean, many of which lead directly to the tissue-pin interface. Infection at this tissue-pin interface can produce serious complications including eventual loosening and failure of the bone anchored mounting post.

There exists, therefore, a significant need for improvements in and to external or exoskeletal prosthetic devices of the type utilizing a bone anchored mounting system, wherein the risk of infection at the soft tissue interface with an externally protruding fixator pin is substantially reduced and/or eliminated. The antimicrobial containment cap of the present invention fulfills these needs and provides further related advantages.

SUMMARY OF THE INVENTION

In accordance with the invention, an antimicrobial containment cap is provided for use in combination with a bone anchored prosthesis mounting system. Such bone anchored mounting system includes an implanted bone anchored mounting post adapted for secure and stable affixation to patient bone, wherein the implanted mounting post carries or is connected to a fixator pin which protrudes through soft skin tissue and the like covering the end or stump of a residual amputated limb and is adapted for secure and stable attachment to an external or exoskeletal prosthesis such as a prosthetic limb or the like. The containment cap is interposed between the external prosthesis and the soft tissue at the end of the residual limb, and carries and retains a selected antimicrobial agent against the amputee's skin in a position generally closely overlying and substantially circumscribing the host tissue exit site or interface between soft tissue and the fixator pin. The containment cap, which is adapted for quick and easy periodic removal for cleaning and/or replenishment of the antimicrobial agent, thus safeguards the tissue-pin interface against infection.

In one preferred form, the containment cap comprises a generally cup-shaped structure having an open-ended configuration defining a cavity adapted for receiving and supporting the selected antimicrobial agent. In a preferred embodiment, the antimicrobial agent may be carried by or embedded or impregnated within a disk-shaped member formed from a relatively soft and resilient material such as a fibrous batting or gauze or foam material having a size and shape for seated reception into the open-ended cap cavity. The containment cap further incorporates fastener means for removable attachment locked onto the external fixator pin, such as a central cylindrical hub depending from a cap base wall. A set screw or the like may be fastened through the depending hub into engagement with the fixator pin, when the containment cap is slidably or rotatably fitted onto the fixator pin with the soft disk-shaped, agent-carrying member contacting or in close proximity to the soft tissue of the residual limb substantially at the tissue-pin interface. The fixator pin protrudes through and beyond the containment cap to define a free end exposed for suitable removable attachment to the associated prosthesis, such as a prosthetic leg or arm for an amputee.

In use, the containment cap closely overlies the soft tissue interface with the externally protruding fixator pin, to retain the antimicrobial agent against and in close proximity with this soft tissue interface throughout normal usage of the prosthesis. The selected antimicrobial agent may comprise any selected medicant in ointment, gel, lotion or other form chosen for killing any selected infection-causing organism or organisms, or other medicant such as a conditioning or anti-inflammation agent or the like. Upon removal of the prosthesis, the containment cap can be quickly and easily removed from the fixator pin for appropriate cleaning of the residual limb soft tissue and/or cap surfaces, as well as replenishment and/or replacement of the infection-preventive agent.

Other features and advantages of the present invention will become apparent from the following more detailed description, taken in connection with the accompanying drawing which illustrate, by way of example, the principals of the present invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
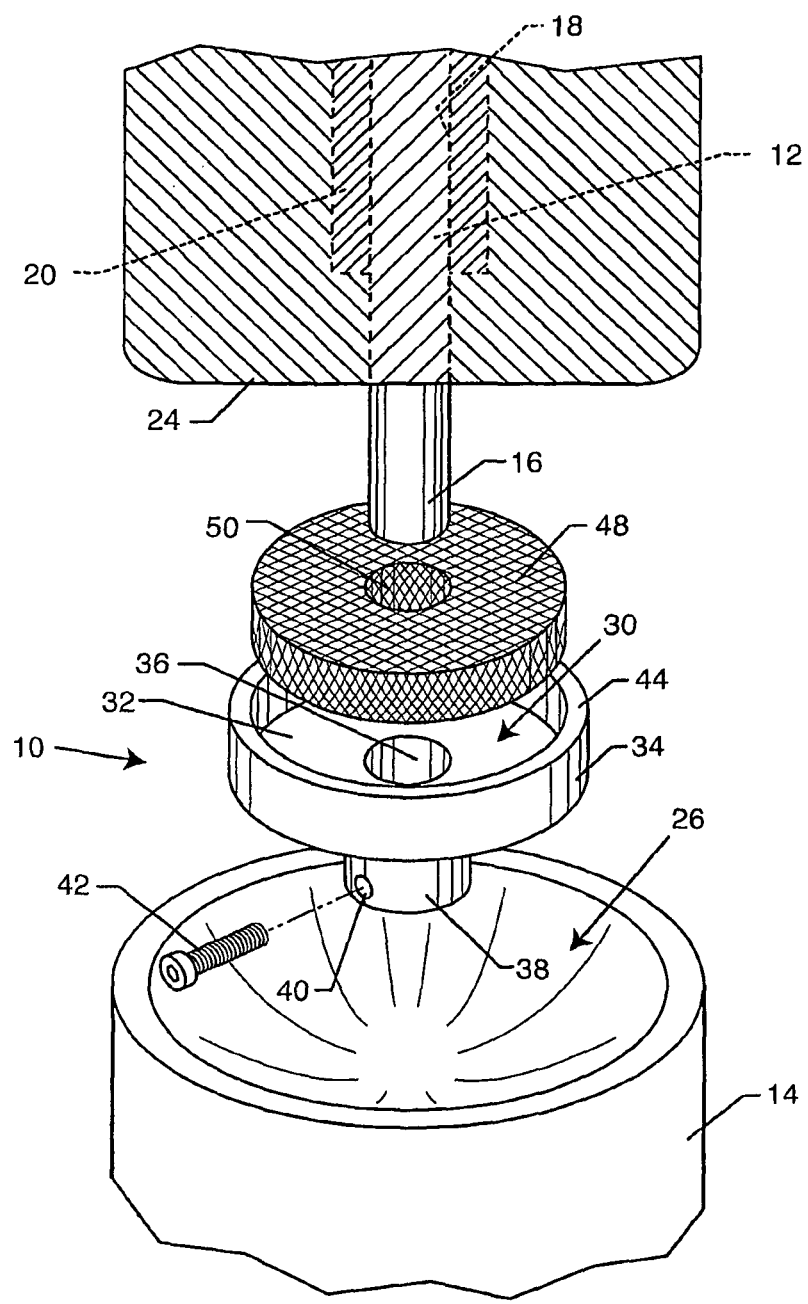
FIG. 1 is an exploded and partially fragmented perspective view showing the antimicrobial containment cap of the present invention in combination with a bone anchored prosthesis mounting post for use in removable external attachment to an exoskeletal prosthesis, such as a prosthetic leg.
Figure 2:
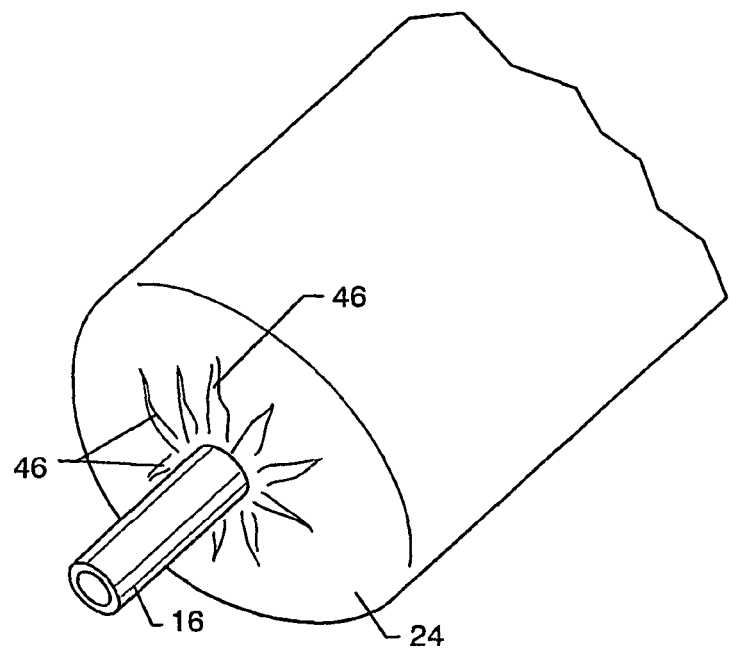
FIG. 2 is a fragmented perspective view illustrating an upper leg portion of a transfemoral amputee, including a bone anchored prosthesis mounting post defining an externally protruding fixator post member for use in removable attachment of an exoskeletal prosthesis.

As shown in the exemplary drawings, an antimicrobial containment cap referred to generally in FIG. 1 by the reference numeral 10 is provided for use with a bone anchored mounting system of the type having an implanted mounting post 12 designed for secure and stable attachment to an external or exoskeletal prosthesis 14, such as a prosthetic limb or the like for an amputee. The containment cap 10 carries and retains a selected medicant in a position for contacting soft tissue substantially at the exit site or tissue interface with an externally protruding fixator pin or post 16 adapted for removable connection to the external prosthesis 14. The containment cap 10 is designed for significantly reducing or eliminating risk of infection at this soft tissue interface with the externally protruding fixator pin 16.

The antimicrobial containment cap 10 of the present invention is particularly designed for use with external or exoskeletal prosthetic fixation or mounting systems of the type having the internal, implanted bone anchored mounting post 12 which is surgically attached to and securely supported by patient bone, as by means of osseointegration or the like. For example, with reference to the illustrative drawings as viewed in FIGS. 1-2 and 4-5, the bone anchored mounting post 12 comprises an elongated tube or rod formed typically from a high strength and biocompatible metal or the like adapted for secure affixation within the intramedullary canal 18 of a long patient bone 20 such as by seated implantation into a lower end of an amputated femur in the case of a transfemoral amputee. The mounting post 12 extends from the amputated end of the patient bone 20 through the adjacent and associated soft tissue 24 which overlies the amputated bone end and defines the stump of the residual amputated limb. Importantly, the mounting post 12 extends further, in a one-piece or multi-piece construction, through this soft tissue 24 of the residual limb to define the externally protruding fixator pin 16 for attachment in any suitable manner (not shown herein) to the exoskeletal prosthesis 14, such as a prosthetic leg in the case of a transfemoral amputee.

The implanted bone anchored mounting post 12 and associated externally protruding fixator pin 16 beneficially accommodate direct mechanical support of the prosthesis 14 and associated direct mechanical loading by the patient bone 20 during normal use such as during ambulatory movements. In other words, such mechanical loads are transmitted from the prosthesis 14 directly via the rigid linkage defined by the fixator pin 16 and the mounting post 12 to the patient bone 20, wherein ambulatory loading is substantially carried by the bone 20 in a normal anatomical manner. By contrast, the soft tissue 24 at the end of the residual limb is substantially unloaded, compressively or otherwise, since the soft tissue 24 is not required to bear or transmit these mechanical loads. As a result, the bone anchored mounting system beneficially provides a more stable and more secure attachment of the prosthesis 14 to the amputee in a manner capable of accommodating more normal and more natural ambulatory movements. By avoiding significant mechanical loading of the soft tissue 24, soft tissue blistering and chafing and other skin irritation problems associated with a traditional soft tissue loaded prosthesis interface are substantially reduced and/or eliminated. In addition, by mechanically linking and supporting the prosthesis 14 from the patient bone 20, amputees have reported a significant increase in perception of the prosthesis 14 as an actual and natural body part—a highly desirable factor referred to as "osseoperception".

The antimicrobial containment cap 10 of the present invention is designed for mounting along the externally protruding portion of the fixator pin 16 substantially at the soft tissue interface with said fixator pin 16, and interposed between the residual limb soft tissue 24 and the associated prosthesis 14. Accordingly, in a preferred orientation as shown, the containment cap 10 may be sized and shaped for substantially nested positioning within an upwardly open socket 26 (FIG. 1) formed in or defined by an upper end of the associated prosthesis 14, whereby the cap 10 is substantially concealed from view during normal use. The containment cap 10 is, in the preferred form, mounted onto the fixator pin 16 but in a manner that does not interfere with the desired direct transfer of mechanical loads by the fixator pin 16 and associated mounting post 12 from the prosthesis 14 to the patient bone 20. In other words, the containment cap 10 may be carried by the fixator pin 16 in a manner that does not result in substantial compressive loads applied to the cap 10 or to the soft tissue 24 of the residual limb. Importantly, the containment cap 10 supports and retains the selected medicant such as an antimicrobial agent in substantial contact or in close proximity with the soft tissue 24, substantially at the tissue interface with the protruding fixator pin 16, to reduce and/or eliminate risk of infection.

Figure 3:
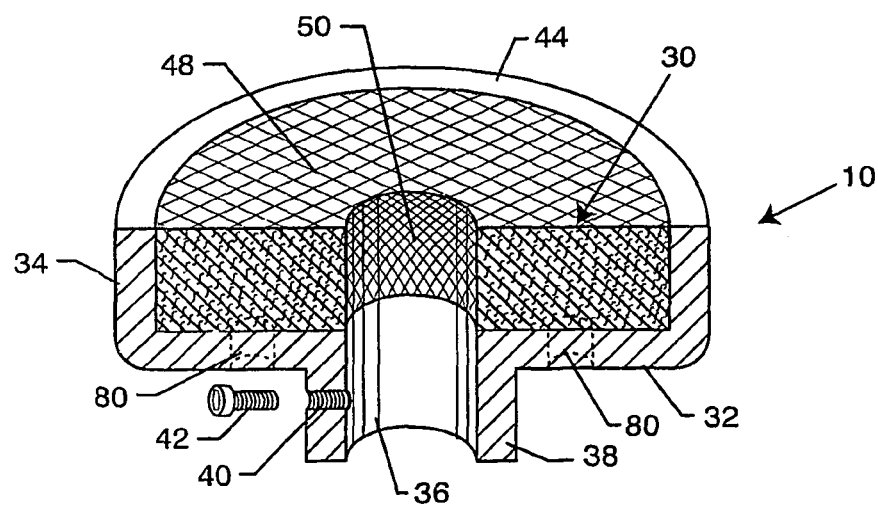
FIG. 3 is an enlarged sectional view of the antimicrobial containment cap of the present invention.
Figure 4:
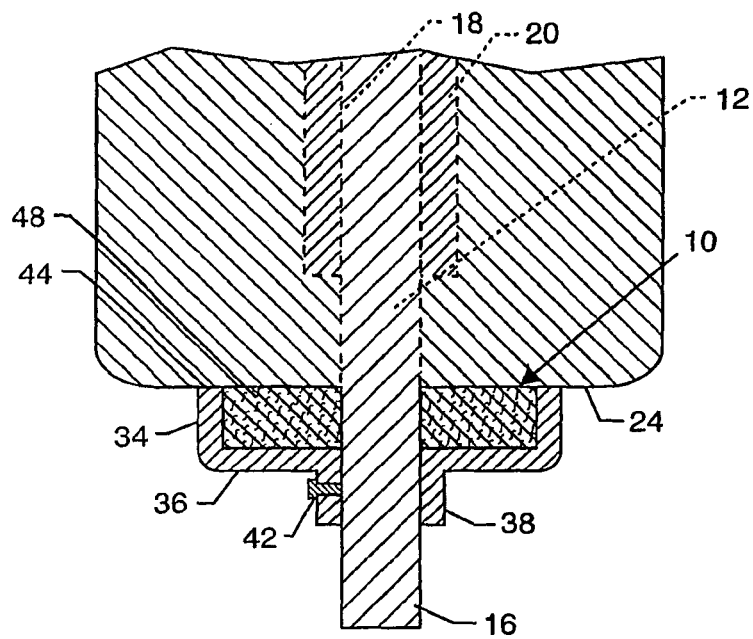
FIG. 4 is an elevation view, shown partially in vertical section, showing the antimicrobrial containment cap mounted onto the externally protruding fixator post.

As shown best in FIGS. 1, 3 and 4, the containment cap 10 comprises (in one preferred form) a substantially cup-shaped body 28 defining an open-ended or upwardly open cavity 30 including a generally circular base wall 32 joined at its perimeter with a short, upstanding side wall 34 of generally cylindrical shape. A central bore 36 is formed in the base wall 32 and defines a passage through a short, vertically oriented mounting hub or mounting collar 38 protruding downwardly therefrom. A radially oriented threaded port 40 is formed in the mounting collar 38 for thread-in reception of a fastener such as a set screw 42 or the like.

In use, the above-described containment cap 10 is mounted onto the exposed end of the fixator pin 16 by slidably fitting the pin 16 through the hub bore 36. The cap 10 is adjustably positioned along the length of the fixator pin 16 to position and preferably seat an upper margin 44 of the side wall 34 firmly but with a relatively light force against the soft tissue 24 of the residual limb. When suitably positioned, the set screw 42 or the like can be appropriately advanced within the threaded port 40 to engage the fixator pin 16, thereby locking the containment cap 10 in place on the fixator pin 16.

Prior to such positional adjustment and positional locking of the containment cap 10 onto the fixator pin 16, the selected medicant such as the selected antimicrobial agent is placed into the cap cavity 30. Accordingly, when the cap 10 is locked onto the fixator pin 16 as described above, the medicant carried thereby is positioned substantially against the soft patient 24 located at and surrounding or circumscribing the soft tissue interface with the fixator pin 16 at the exit site of the pin 16 from the tissue 24 at the end of the residual limb. Importantly, since this soft tissue 24 typically incorporates numerous relatively small or shallow ridges and folds and associated intervening channels 46 (FIG. 2) extending typically in a generally radial direction relative to the fixator pin 16, and thus defining typically hard-to-clean pathways leading to the pin-tissue interface, the presence of the medicant at this location beneficially deters and/or eliminates risk of undesirable infection.

In the preferred form, the antimicrobial agent can be carried by and/or embedded within a soft and resilient member 48 such as a disk-shaped fibrous or gauze or foam pad. Such pad 48 may be formed with a size and shape for slide-fit reception into the cap cavity 30, and may include a central bore 50 for slide-fit reception over the fixator pin 16 as the containment cap 10 is mounted thereon. The pad 48 may have a thickness for slight compression against the soft tissue 24 upon final positioning of the cap 10, thereby insuring relatively intimate medicant contact with the pin-tissue interface.

The selected medicant such as the selected antimicrobial agent may be provided in any convenient form such as an ointment or gel or salve or the like, suitable for carrying by the soft pad 48 against the soft tissue 24. Various medicants may be used, such as antibacterial or antibiotic compounds and/or combinations thereof suitable for killing infection-causing organisms at the pin-tissue interface. Alternative medicants can be used, including but not limited to conditioning or anti-inflammation agents and the like.

Upon periodic and typically normal removal of the prosthesis 14 from the fixator pin 16, the containment cap 10 can be removed quickly and easily from the fixator pin 16 for convenient cleaning and/or replenishment of the medicant and/or soft pad 48, or alternately for disposal and replacement of these components. In this regard, the containment cap 10 may be constructed from a metal material suitable for cleaning and re-use, or alternately from a lightweight plastic material or the like conducive to single usage followed by disposal. The soft pad 48 may also be designed for cleaning and re-use with medicant replenishment, or alternately for single usage and disposal. When removed from the fixator pin 16, the soft tissue 24 is conveniently exposed for cleaning.

Figure 5:
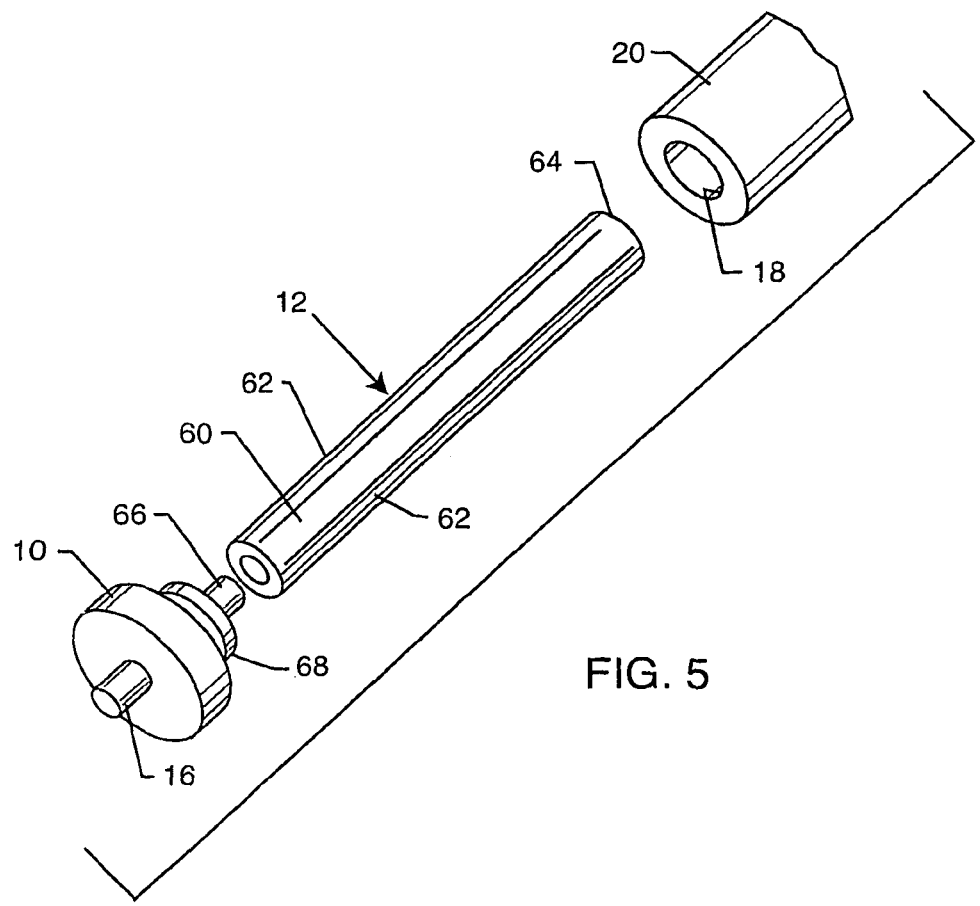
FIG. 5 is an exploded and partially fragmented perspective view depicting surgical implantation of the bone anchored mounting post.

FIG. 5 depicts one preferred form for the bone anchored mounting post 12 and associated fixator pin 16 with the containment cap 10 for assembly therewith. As shown, the bone anchored mounting post 12 comprises an elongated and generally tubular component 60 having longitudinally extending external flutes 62 formed thereon, and a closed upper end 64. Outer surfaces of the post 12 may be constructed to include porous bone ingrowth surfaces (not shown) for improved osseointegration, if desired. This mounting post 12 is sized and shaped for suitable surgical implantation and secure affixation within the medullary canal 18 of the patient bone 20, such as an amputated femur. Persons skilled in the art, however, will recognize and appreciate that alternative mounting post configurations and affixation techniques, including but not limited to thread-in post structures, may be used.

The fixator pin 16 shown in FIG. 5 includes an upper end 66 having a suitable size and configuration for seated reception and secure affixation as by press-fitting into the open lower end of the post 12. A radially enlarged flange 68 may be formed on the pin 16 to provide an enlarged and stable stop for seating against the lower end of the amputated bone 20. The fixator pin 16 protrudes coaxially with the implanted anchoring post 12 downwardly from the stop flange 68 for passage through the soft tissue 24 (FIGS. 1, 2 and 4) at the end of the residual limb, and appropriate removable attachment of the containment cap 10 and associated prosthesis 14, as previously shown and described herein. As shown, this externally protruding end of the fixator pin 16 may have a noncircular cross sectional shape, such as the squared cross sectional shape as shown in FIG. 5, for suitable secure attachment to the external prosthesis 14 (not shown).

Figure 6:
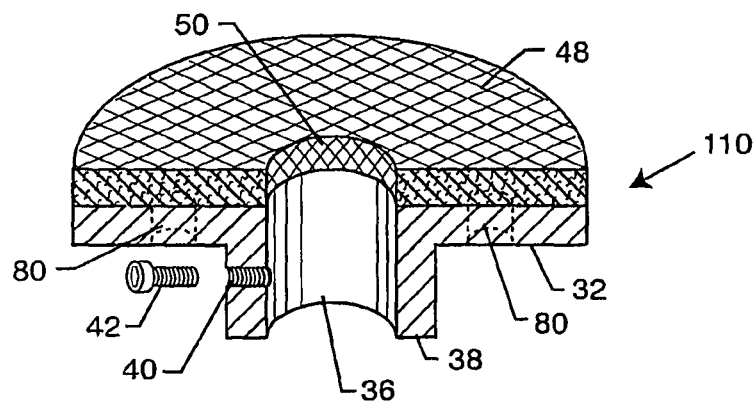
FIG. 6 is an enlarged sectional view similar to FIG. 3, but illustrating one alternative preferred form of the invention.
Figure 7:
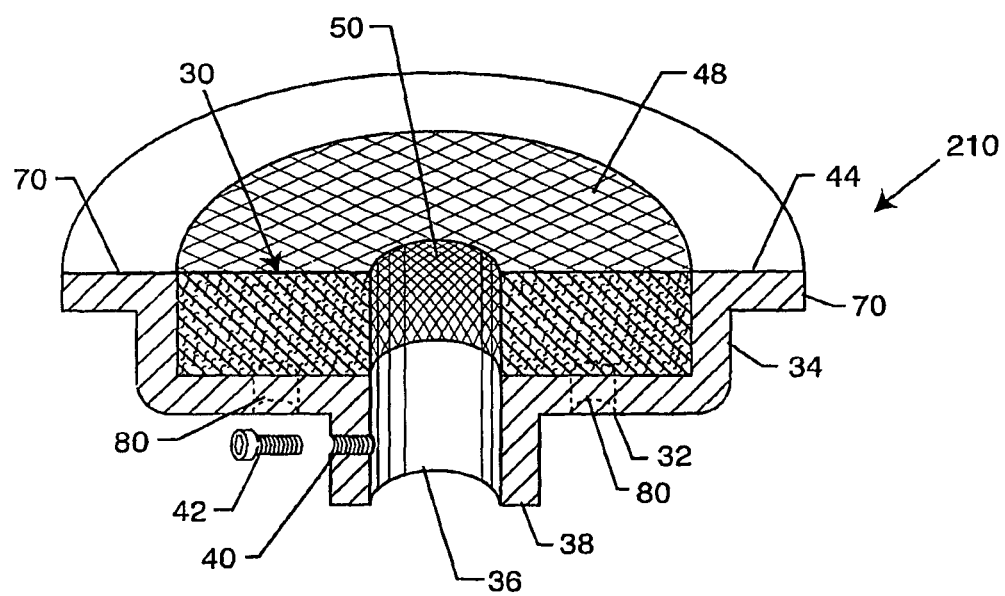
FIG. 7 is an enlarged sectional view similar to FIGS. 3 and 6, but showing a further alternative preferred form of the invention.

FIGS. 6 and 7 illustrate alternative preferred forms of the containment cap 10 of the present invention, wherein components corresponding with those shown and described in FIGS. 1-5 are identified by common reference numerals. In this regard, FIG. 6 illustrates one preferred alternative containment cap configuration 110, wherein the disk-shaped and medicant-supporting soft pad 48 is carried by a circular base wall 32 in the absence of an upstanding cylindrical side wall 34 of the type shown and described in FIGS. 1, 3 and 4. FIG. 7 shows another alternative preferred containment cap form 210 constructed according to FIGS. 1, 3 and 4 but wherein the upper margin 44 of an upstanding cap side wall 34 merges with a radially outwardly extending support flange 70 defining a broad-based surface area for contacting the soft tissue 24 at the end of the residual limb. In both embodiments of FIGS. 6 and 7, the modified containment caps 110 and 210 are adapted for removable mounting onto the fixator pin 16 in substantially the same manner as previously shown and described, to support and retain the soft pad 48 and associated antimicrobial agent carded thereby against the pin-tissue interface.

Although various embodiments and alternatives have been described in detail for purposes of illustration, various further modifications may be made without departing from the scope and spirit of the invention. For example, although shown and described in connection with a bone anchored mounting post protruding from the patient's body, persons skilled in the art will recognize and appreciate that the containment cap may be used with other rigid and nonrigid structures protruding from the human body. By way of further example, it will be recognized and appreciated that the containment cap may incorporate vented ports as depicted in dotted lines by reference numeral 80 in FIGS. 3, 6 and 7 to accommodate air flow to and ventilation of the pin-tissue interface. Accordingly, no limitation on the invention is intended by way of the foregoing description and accompanying drawings, except as set forth in the appended claims.

What is claimed is:

1. An exoskeletal prosthesis system comprising:
a bone anchored mounting post with a fixator structure protruding from the mounting post through soft tissue at the end of a residual limb and defining a free end for attachment to a prosthesis;
a socket formed in an upper end of the prosthesis; and
a containment cap including a cap body having a bore formed therein for removable slide-fit placement of said cap body onto the external fixator structure, said cap body being adapted to be positioned between the prosthesis and the soft tissue at the end of the residual limb, said cap body at least partially positioned within the socket at an upper end of the prosthesis, and
a resilient member carried by said cap body in a position closely overlying and substantially circumscribing an interface between the soft tissue at the end of the residual limb and the fixator structure, the resilient member supporting a medicant selected from the group consisting essentially of an antimicrobial agent, an antibacterial agent, an anti-inflammation agent, and combinations thereof.

2. The exoskeletal prosthesis system of claim 1 further including means for removably attaching said cap body to the fixator structure.

3. The exoskeletal prosthesis system of claim 2 wherein said cap body comprises a base wall having a central bore formed therein, and further wherein said means for removably attaching said cap body to the fixator structure comprises a hollow mounting hub depending from said base wall for slide-fit reception of the fixator structure, and fastener means for removably locking said hub relative to the fixator structure.

4. The exoskeletal prosthesis system of claim 3 wherein the resilient member includes a thickness for at least some compression when said mounting hub is removably locked to the fixator structure.

5. The exoskeletal prosthesis system of claim 3 wherein said cap body further defines a perimeter wall upstanding from said base wall, said perimeter wall defining an upper margin for contacting the soft tissue at the end of the residual limb when said mounting hub is removably locked to the fixator structure.

6. The exoskeletal prosthesis system of claim 5 wherein said perimeter wall upper margin further comprises a radially outwardly extending support flange for contacting the soft tissue at the end of the residual limb when said mounting hub is removably locked to the fixator structure.

7. The exoskeletal prosthesis system of claim 6 wherein said cap body has at least one vent port formed therein.

8. An exoskeletal prosthesis system comprising:
a bone anchored mounting post with a fixator structure protruding from the mounting post through soft tissue at the end of a residual limb and defining a free end for attachment to a prosthesis;
a socket formed in an upper end of the prosthesis; and
a containment cap including a cap body having a bore formed therein for slide-fit placement of said cap body onto the external fixator structure, said cap body being adapted to be positioned between the prosthesis and the soft tissue at the end of the residual limb, said cap body at least partially positioned within the socket at an upper end of the prosthesis, and
a resilient member carried by said cap body in a position closely overlying and substantially circumscribing an interface between the soft tissue at the end of the residual limb and the fixator structure, the resilient member supporting a medicant selected from the group consisting essentially of an antimicrobial agent, an antibacterial agent, an anti-inflammation agent, and combinations thereof; and
fastener means for removably locking said cap body relative to the fixator structure.

9. The exoskeletal prosthesis system of claim 8 wherein said cap body comprises a base wall having a central bore formed therein, and further wherein said fastener means comprises a hollow mounting hub depending from said base wall for slide-fit reception of the fixator structure, and at least one fastener for removably locking said hub relative to the fixator structure.

10. The exoskeletal prosthesis system of claim 9 wherein the resilient member includes a thickness for at least some compression when said mounting hub is removably locked to the fixator structure.

11. The exoskeletal prosthesis system of claim 9 wherein said cap body further defines a perimeter wall upstanding from said base wall, said perimeter wall defining an upper margin for contacting the soft tissue at the end of the residual limb when said mounting hub is removably locked to the fixator structure.

12. The exoskeletal prosthesis system of claim 11 wherein said perimeter wall upper margin further comprises a radially outwardly extending support flange for contacting the soft tissue at the end of the residual limb when said mounting hub is removably locked to the fixator structure.

* * * * *

UNITED STATES PATENT AND TRADEMARK OFFICE
CERTIFICATE OF CORRECTION

PATENT NO. : 8,444,701 B2  Page 1 of 1
APPLICATION NO. : 11/995886
DATED : May 21, 2013
INVENTOR(S) : Bloebaum et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1522 days.

Signed and Sealed this
Eighth Day of September, 2015

Michelle K. Lee
*Director of the United States Patent and Trademark Office*

UNITED STATES PATENT AND TRADEMARK OFFICE
CERTIFICATE OF CORRECTION

PATENT NO.        : 8,444,701 B2
APPLICATION NO.   : 11/995886
DATED             : May 21, 2013
INVENTOR(S)       : Roy D. Bloebaum et al.

Page 1 of 1

It is certified that error appears in the above-identified patent and that said Letters Patent is hereby corrected as shown below:

In the Specification

Column 1, Line 5, after the title, please insert the following:
-- STATEMENT REGARDING FEDERALLY SPONSORED RESEARCH OR DEVELOPMENT
This invention was made with government support under Grant Number W81XWH-05-1-0628 awarded by ARMY/MRMC – Medical Research and Materiel Command. The government has certain rights in the invention. --

Signed and Sealed this
Thirteenth Day of August, 2019

Andrei Iancu
*Director of the United States Patent and Trademark Office*